(12) United States Patent
Ferrari et al.

(10) Patent No.: US 9,066,924 B2
(45) Date of Patent: *Jun. 30, 2015

(54) ELLAGITANNINS RICH EXTRACTS COMPOSITION IN SEXUAL WELLNESS

(71) Applicant: Horphag Research IP (QR) LTD, Limassol (CY)

(72) Inventors: Victor Ferrari, Cointrin (CH); Frank Schoenlau, Münster (DE); Carolina Burki, Cointrin (CH)

(73) Assignee: HORPHAG RESEARCH IP (QR) LTD, Limassol (CY)

( * ) Notice: Subject to any disclaimer, the term of this patent is extended or adjusted under 35 U.S.C. 154(b) by 0 days.

This patent is subject to a terminal disclaimer.

(21) Appl. No.: 14/366,386

(22) PCT Filed: Dec. 21, 2012

(86) PCT No.: PCT/EP2012/076837
§ 371 (c)(1),
(2) Date: Jun. 18, 2014

(87) PCT Pub. No.: WO2013/093096
PCT Pub. Date: Jun. 27, 2013

(65) Prior Publication Data
US 2014/0343134 A1   Nov. 20, 2014

(30) Foreign Application Priority Data

Dec. 23, 2011 (CH) ....................... 2045/11

(51) Int. Cl.
| | | |
|---|---|---|
| A61K 36/40 | (2006.01) |
| A61K 36/44 | (2006.01) |
| A61K 36/49 | (2006.01) |
| A61K 31/357 | (2006.01) |
| A61K 31/7024 | (2006.01) |
| A61K 45/06 | (2006.01) |
| A61K 31/365 | (2006.01) |
| A23L 1/30 | (2006.01) |

(52) U.S. Cl.
CPC ........... *A61K 31/357* (2013.01); *A61K 31/7024* (2013.01); *A61K 36/49* (2013.01); *A61K 45/06* (2013.01); *A61K 31/365* (2013.01); *A23L 1/3002* (2013.01); *A23V 2002/00* (2013.01)

(58) Field of Classification Search
CPC ...................................................... A61K 36/49
See application file for complete search history.

(56) References Cited

U.S. PATENT DOCUMENTS 8,372,454 B2 * 2/2013 Aviram et al. ................ 424/769
2004/0247698 A1 * 12/2004 Valenzuela Cortes ........ 424/725

FOREIGN PATENT DOCUMENTS

WO    WO-2011/161655 A1    12/2011

OTHER PUBLICATIONS

Larrosa et al. (2010) Molecular Aspects of Medicine 31, 513-539.*
Raskin et al. (2004) Current Phamaceutical Design, 10, 3419-3429.*
Revilla et al. (1998) J. Agric. Food Chem. 46, 4592-4597.*
Bhattacharya, D. (2011) "Fight Malaria at home: Therapeutic and prophylaxis clinical data", *Asian Pacific Journal of Tropical Disease*, 1(2): 142-149.
International Preliminary Report on Patentability dated Apr. 2, 2014 issued in PCT Application No. PCT/EP2012/076837.
International Preliminary Report on Patentability dated Apr. 22, 2014 issued in PCT Application No. PCT/EP2012/076845.
International Search Report dated Apr. 16, 2013 issued in PCT Application No. PCT/EP2012/076845.
International Search Report dated Apr. 11, 2013 issued in PCT Application No. PCT/EP2012/076837.
Khallouki, F., et al. (2007) "Isolation, purification and identification of ellagic acid derivatives, catechins, and procyanidins from the root bark of *Anisophyllea dichostyla* R. Br", *Food Chem Toxicol*, 45(3): 472-485.
Larrosa, M., et al. (2010) "Ellagitannins, ellagic acid and vascular health", *Molecular Aspects of Medicine*, 31(6):513-539.
Written Opinion of the International Preliminary Examining Authority dated Nov. 19, 2013 issued in PCT Application No. PCT/EP2012/076837.
Office Action dated Oct. 27, 2014 issued in U.S. Appl. No. 14/366,385.

* cited by examiner

*Primary Examiner* — Chris R Tate
*Assistant Examiner* — Russell Fiebig
(74) *Attorney, Agent, or Firm* — Harness, Dickey & Pierce, P.L.C.

(57) ABSTRACT

The present invention relates to a composition consisting of ellagitannins rich extracts originated from plant extracts of the Fagaceae family, for use in a method for improving sexual fitness or wellness of both sexes, the male sexual enhancement, the treatment of sexual dysfunction and the health of the sexual vascular system of both sexes.

19 Claims, No Drawings

ELLAGITANNINS RICH EXTRACTS COMPOSITION IN SEXUAL WELLNESS

PRIORITY STATEMENT

This application is a national stage application under 35 U.S.C. §371 of PCT International Application No. PCT/EP2012/076837, which has an international filing date of 21 Dec. 2012 and claims priority under 35 U.S.C. §119 to Switzerland Application No. 02045/11 filed 23 Dec. 2011. The contents of each application recited above are incorporated herein by reference in their entirety.

FIELD OF THE INVENTION

The present invention relates to a composition consisting of ellagitannins rich extracts originated from plant extracts of the Fagaceae family, for use in a method for improving sexual fitness or wellness of both sexes, the male sexual enhancement, the treatment or prevention of sexual dysfunction and the health of the sexual vascular system of both sexes.

BACKGROUND OF THE INVENTION

When a male is in his early twenties, it's easy to take peak sexual performance for granted. Yet as time passes, the male body's biological system changes, and he may notice that his sexual stamina, performance and even pleasure begin to decrease. Getting "in the mood" may start to take a little effort.

Many women have problems with sex when they reach menopause and their ovaries produce smaller amounts of sex hormones. Lower levels of estrogen can make the vaginal tissue dry, and less androgen leads to less sexual desire and arousal. One important difference affecting sexual desire is that men have levels of testosterone that are 20 to 30 times what women have. Men's testosterone levels gradually decline over time but they do not experience a drop-off as women do at menopause. In men and women, testosterone and other androgens work to increase desire.

Treatment with drugs, such as those used for hypertension and hyperlipidemia, may have negative effects on sexual function and interest. Vaginal dryness is progressively more frequent with age, and vaginal infections are more common with increasing age and in diabetic women. They may cause sexual dysfunction (SD), loss of interest, and difficult or painful intercourse that can be associated with anxiety and fear, contributing to a lack of motivation.

The family Fagaceae, or beech family, comprises about 900 species of both evergreen and deciduous trees and shrubs, which are characterized by alternate simple leaves with pinnate venation, unisexual flowers in the form of catkins, and fruit in the form of cup-like (cupule) nuts. Fagaceous leaves are often lobed and both petioles and stipules are generally present. Fruits lack endosperm and lie in a scaly or spiny husk that may or may not enclose the entire nut, which may consist of one to seven seeds. The best-known group of this family is the oaks, genus *Quercus*, the fruit of which is a non-valved nut (usually containing one seed) called an acorn. The husk of the acorn in most oaks only forms a cup in which the nut sits.

Several members of the Fagaceae have important economic uses. Many species of oak, chestnut, and beech (genera *Quercus*, *Castanea*, and *Fagus* respectively) are commonly used as timber for floors, furniture, cabinets, and wine barrels. Cork for stopping wine bottles and a myriad of other uses is made from the bark of cork oak, *Quercus suber*. Chestnuts, a tasty treat enjoyed by many in the winter, are the fruits from species of the genus *Castanea*. Numerous species from several genera are prominent ornamentals, and wood chips from the genus *Fagus* are often used in flavoring beers.

There is still a need for an effective, natural and safe composition for improving sexual fitness or wellness of both sexes, the man sexual enhancement, the treatment of sexual dysfunction.

SUMMARY OF THE INVENTION

In one aspect of the present invention there is provided a composition consisting of ellagitannins rich extracts originated from plant extracts of the Fagaceae family, for use in a method for improving sexual fitness or wellness of both sexes, the male sexual enhancement, the treatment or prevention of sexual dysfunction and the health of the sexual vascular system of both sexes.

Another aspect of the invention resides in a composition that, when administered, offers both sex a safe, natural way to preserve and maintain sexual responsiveness, endurance and enjoyment. It includes a blend or composition consisting of ellagitannins rich extracts originated from plants of the Fagacaea family. When the blend is administered, or taken on a daily basis over a period of time, sexual fitness or sexual wellness improves by the end of the period of time.

In another aspect, the present invention provides for a dietary or food supplement, a food preparation, a beverage, a medicament and a topical preparation comprising the composition of the present invention.

In a further aspect, the composition of the present invention is provided for improving sexual fitness or wellness of both sexes, the man sexual enhancement, the treatment of sexual dysfunction and the health of the sexual vascular system of both sexes.

DETAILED DESCRIPTION OF THE INVENTION

Although methods and materials similar or equivalent to those described herein can be used in the practice or testing of the present invention, suitable methods and materials are described below. All publications, patent applications, patents, and other references mentioned herein are incorporated by reference in their entirety. The publications and applications discussed herein are provided solely for their disclosure prior to the filing date of the present application. Nothing herein is to be construed as an admission that the present invention is not entitled to antedate such publication by virtue of prior invention. In addition, the materials, methods, and examples are illustrative only and are not intended to be limiting.

In the case of conflict, the present specification, including definitions, will control. Unless defined otherwise, all technical and scientific terms used herein have the same meaning as is commonly understood by one of skill in art to which the subject matter herein belongs. As used herein, the following definitions are supplied in order to facilitate the understanding of the present invention.

The term "comprise" is generally used in the sense of include, that is to say permitting the presence of one or more features or components.

As used in the specification and claims, the singular form "a", "an" and "the" include plural references unless the context clearly dictates otherwise.

The term "extract", as used herein includes any preparation obtained from plants, fruits, roots or vegetables using an extraction method.

The term "food preparation" refers generally to material of either plant or animal origin, or of synthetic sources, that contain essential nutrients such as a carbohydrate, protein, fat, vitamin, mineral, etc. used in the body of an organism to sustain growth, repair, and vital processes and to furnish energy.

A "dietary or food supplement" refers to a product that contains substances like vitamins, minerals, foods, botanicals, amino acids and is intended to supplement the usual intake of these substances. Dietary supplements are found in pill, tablet, capsule, powder or liquid form and are meant to be taken by mouth.

The term "nutraceutical" refers to any substance that is a food or a part of a food and provides medical or health benefits, including the prevention and treatment of disease. Such products may range from isolated nutrients, dietary supplements and specific diets to genetically engineered designer foods, herbal products, and processed foods such as cereals, soups and beverages. It also refers to a product isolated or purified from foods, and generally sold in medicinal forms not usually associated with food and demonstrated to have a physiological benefit or provide protection against diseases like chronic diseases for example.

The term "beverage" means a liquid for drinking, which may be water, flavored water, soft drinks, alcoholic drink, health drink, or an enriched drink like based on a diary product (milk) or fruit juice.

"Pharmaceutically acceptable excipients or carriers" are any materials that do not interfere with the pharmacological activity of the active ingredient(s) or degrade the body functions of the subject to which it can be administered but facilitate fabrication of dosage forms or administration of the composition. Examples of pharmaceutically acceptable excipient include but are not limited to maltodextrin, calcium phosphate, and fused silica. Pharmaceutically acceptable excipients also include flavorants, as well as various additives such as other vitamins and minerals, all solvents, dispersion media, coatings, isotonic and absorption delaying agents, sweeteners and the like, non-toxic auxiliary substances such as wetting or emulsifying agents, pH buffering agents and the like, such as for example, sodium acetate, sorbitan monolaurate, triethanolamine oleate, and inert ingredients such as talc and magnesium stearate which are standard excipients in the manufacture of tablets, capsules and other dosage forms.

As used herein the terms "subject" or "patient" are well-recognized in the art, and, are used interchangeably herein to refer to a mammal, including dog, cat, rat, mouse, monkey, cow, horse, goat, sheep, pig, camel, and, most preferably, a human. In some embodiments, the subject is a subject in need of treatment or a subject with a disease or disorder. However, in other embodiments, the subject can be a normal subject. The term does not denote a particular age or sex. Thus, adult and newborn subjects, whether male or female, are intended to be covered.

The term "an effective amount" refers to an amount necessary to obtain a physiological effect. The physiological effect may be achieved by one application dose or by repeated applications. The dosage administered may, of course, vary depending upon known factors, such as the physiological characteristics of the particular composition; the age, health and weight of the subject; the nature and extent of the symptoms; the kind of concurrent treatment; the frequency of treatment; and the effect desired and can be adjusted by a person skilled in the art.

As used herein, the terms "prevention" and "preventing," when referring to a disorder or symptom, refers to a reduction in the risk or likelihood that a mammalian subject will develop said disorder, symptom, condition, or indicator after treatment according to the invention, or a reduction in the risk or likelihood that a mammalian subject will exhibit a recurrence of said disorder, symptom, condition, or indicator once a subject has been treated according to the invention and cured or restored to a normal state.

As used herein, the terms "treatment" or "treating," when referring to sexual dysfunction, sexual fitness or wellness, sexual enhancement in both sexes, refers to inhibiting or reducing the progression, nature, or severity of the subject condition or delaying the onset of the condition.

The present invention provides a composition consisting of ellagitannins rich extracts originated from plant extracts of the Fagaceae family, for use in a method for treating or preventing sexual dysfunction, for improving sexual fitness or wellness, for improving sexual enhancement in both sexes.

Ellagitannins of the invention are originated from a plant extract or from a synthesized material.

Preferably said ellagitannins rich extracts originated from plant extracts of the Fagacaea family comprise Roburins or derivatives thereof as defined below.

Most preferably the plant extracts of the Fagacaea family consists of *Quercus robur* extracts as defined above.

Another aspect of the invention resides in a composition that, when administered, offers both sex a safe, natural way to preserve and maintain sexual responsiveness, endurance and enjoyment. In particular, the invention also concerns a method for improving the health of the sexual vascular system of both sexes comprising administering to a subject in need thereof an effective amount of ellagitannins rich extracts originated from plant extracts of the Fagacaea family comprising Roburins or derivatives thereof.

Also encompassed by the present invention is a method for improving sexual fitness or wellness of both sexes comprising administering to a subject in need thereof an effective amount of the composition or the medicament of the invention.

The invention also provides for a method for improving man and female sexual enhancement comprising administering to a subject in need thereof an effective amount of the composition or the medicament of the invention.

The invention also concerns a method of treating or preventing sexual dysfunction in both sexes comprising administering to a subject in need thereof an effective amount of the preparation or the medicament according to the invention.

The methods according to the invention enhance a level of sexual wellness for both sexes. The composition of the invention being in therapeutically effective amounts so that, when the composition is administered at least daily over a period of time, in a sufficient amount, it enhances a level of sexual wellness by an end of the period of time.

The methods of the invention also help in attaining enhanced sexual wellness. The administering includes initially administering an elevated dosage of the composition of the invention to attain the enhanced level of sexual wellness by the end of the period of time and thereafter administering a dosage of the composition daily that contains less of the composition than the elevated dosage and still provide the enhanced level of sexual wellness.

"Fitness", whether "sexual fitness" or physical fitness, is defined as a measure of efficient functioning. A person who is sexually fit is efficient in their capacity to think, feel, and behave in a sexual manner without shame, embarrassment, or hidden agendas of falsely boosting their ego or self-esteem. People who reach and practice this style of fitness are more likely to function efficiently in all aspects of their perceptual world. These fortunate individuals are more confident, physically ill less often, and manage stressful events more successfully. Sexual fitness is an achieved state of being allowing people to perform better in every action they engage in. Having this capability affords person to feel confident in all situations whether a partner is involved or not.

"Sexual wellness" of both sexes is the active participation of the individual in his or her life by addressing the numerous issues within sexual health. The process defined as sexual wellness is to improved sexual health. "Sexual health" is a state of physical, mental and social well-being in relation to sexuality. It requires a positive and respectful approach to sexuality and sexual relationships, as well as the possibility of having pleasurable and safe sexual experiences, free of coercion, discrimination and violence (definition WHO 2002). In particular, Sexual health is the integration of the somatic, emotional, intellectual, and social aspects of sexual being, in ways that are positively enriching and that enhance personality, communication, and love. Fundamental to this concept are the right to sexual information and the right to pleasure (definition of WHO 1975). Sexual health is inextricably bound to both physical and mental health.

"Male sexual enhancement" may be defined as the increase of the hardness of erection; the improvement of self-confidence; the improvement of sperm quality, count and motility (spontaneous motion) and fertility; the increase of libido and sex drive; the boosting of the sexual energy level and vitality; the improvement of sexual performance problems i.e. those due to aging as well as the increase of energy and the greater sexual satisfaction with a partner. Men's sexual function is scored using the established "International Index of Erectile Function" (IIEF) questionnaire [Rosen et al, *Urology*. 1997 June; 49(6):822-30. *The international index of erectile function (IIEF): a multidimensional scale for assessment of erectile dysfunction*], see i.e. example 4. http://www.seekwellness.com/mensexuality/questionnaire.htm "Female sexual enhancement" is defined as anything that enhances a woman's sexuality; this includes in particular the increase of libido or sex drive. Low libido or sex drive in women can be caused by a number of factors that vary from one woman to another; fatigue, mild depression, and the multiple roles that women play in daily life can cause psychological issues, which can have an affect on a woman's sexual appetite. Antidepressants, birth control, tranquilizers and mood stabilizers also impact sexual activity and other conditions like diabetes, heart disease and a poor diet can also reduce a woman's sex drive. Woman's sexuality level may be determined by the Female Sexual Function Index (FSFI) and the Women's Health Questionnaire (WHQ) which are defined and detailed in example 4.

"Sexual dysfunction" or sexual malfunction in both sexes refers to a difficulty experienced by an individual or a couple during any stage of a normal sexual activity, including desire, arousal or orgasm. Sexual desire disorders or decreased libido are characterized by a lack or absence for some period of time of sexual desire or libido for sexual activity or of sexual fantasies. Sexual arousal disorders were previously known as frigidity in women and impotence in men, though these have now been replaced with less judgmental terms. Impotence is now known as erectile dysfunction, and frigidity has been replaced with a number of terms describing specific problems with, for example, desire or arousal. For both men and women, these conditions can manifest themselves as an aversion to, and avoidance of, sexual contact with a partner. In men, there may be partial or complete failure to attain or maintain an erection, or a lack of sexual excitement and pleasure in sexual activity.

"Erectile dysfunction" or impotence is a sexual dysfunction characterized by the inability to develop or maintain an erection of the penis. The causes of erectile dysfunction may be psychological or physical.

Orgasm disorders are persistent delays or absence of orgasm following a normal sexual excitement phase. The disorder can have physical, psychological, or pharmacological origins.

Sexual pain disorders affect women almost exclusively and are known as dyspareunia (painful intercourse) or vaginismus (an involuntary spasm of the muscles of the vaginal wall that interferes with intercourse).

While drugs for sexual enhancement may offer a temporary solution or tempting "quick fix," they are associated with unwanted side effects and can be expensive. The blend/composition according to the present invention, which is a natural dietary supplement, offers a safe, natural and cost-effective alternative.

Those plant extracts of the composition according to the present invention are also referred as "ellagitannins rich extracts".

The ellagitannins are a diverse class of hydrolyzable tannins, a type of polyphenol formed primarily from the oxidative linkage of galloyl groups in 1,2,3,4,6-Pentagalloyl glucose. Ellagitannins differ from gallotannins, in that their galloyl groups are linked through C—C bonds, whereas the galloyl groups in gallotannins are linked by depside bonds. Ellagitannins comprise (Roburins A, B, C, D, E, Vescalin, Castalin, Vescalagin, Castalagin).

Preferably said ellagitannins rich extracts originated from plant extracts of the Fagacaea family comprise Roburins or derivatives thereof. Roburins include Roburins A, B, C, D, E In the present invention the term "Roburins" will be considered as equivalent to Roburins A, B, C, D, E and are interchangeable. Roburin A is a tannin found for example in oak wood (*Quercus robur* and *Quercus petraea* or *Quercus alba*) or oak cork (*Quercus suber*). It is a dimeric compound, composed of two vescalagin subunits probably linked through an ether bond between the diphenoyl group of one subunit and the triphenoyl moiety of the other one.

Preferably the plant extracts of the Fagacaea family are selected among genera *Quercus, Castanea*, and *Fagus* or mixtures thereof. Among the Fagaceae, particularly worthy of mention are the *Fagus grandifolia*, common beech (*Fagus sylvatica*), sweet chestnut (*Castanea sativa*) and English oak (*Quercus robur*).

Most preferably, the plant extracts of the Fagacaea family consists of oak woods extracts.

Even more preferably, the plant extracts of the Fagacaea family consists of *Quercus robur* extracts.

"*Quercus robur*" also know as "oak wood" belongs to the family of Fagaceae and the genus *Quercus*. *Quercus robur* (sometimes considered *Q. pedunculata*) is commonly known as Pedunculate oak or English oak. Also included in this definition of "oak wood" is the white oak, *Quercus alba, Quercus brutia* Tenore, *Q. pedunculiflora, Q. haas* as well as the Sessile Oak (*Q. petraea*). In the present invention the term "*Quercus robur*" will be considered as equivalent to oak wood as defined above, they are interchangeable.

Gathering: felling of the trees under National Forest Office control, from October to April when the sap is down. Oak wood is traditionally used to make wine barrels and is known to give its taste to wine and to contribute to its antioxidant activity. Fresh wood chips used for Biolandes extract are purchased from a famous wine barrel maker (http://www.dargaud-jaegle.com/) and obtained from Oak trees rigorously selected.

The extraction process is carried out by water extraction at low temperature (50° C.) and spray drying. No petrochemical solvent is used.

Oak wood extract contains ellagitannins (Roburins A, B, C, D, E, Vescalin, Castalin, Vescalagin, Castalagin) and phenolic acids (gallic acid, ellagic acid).

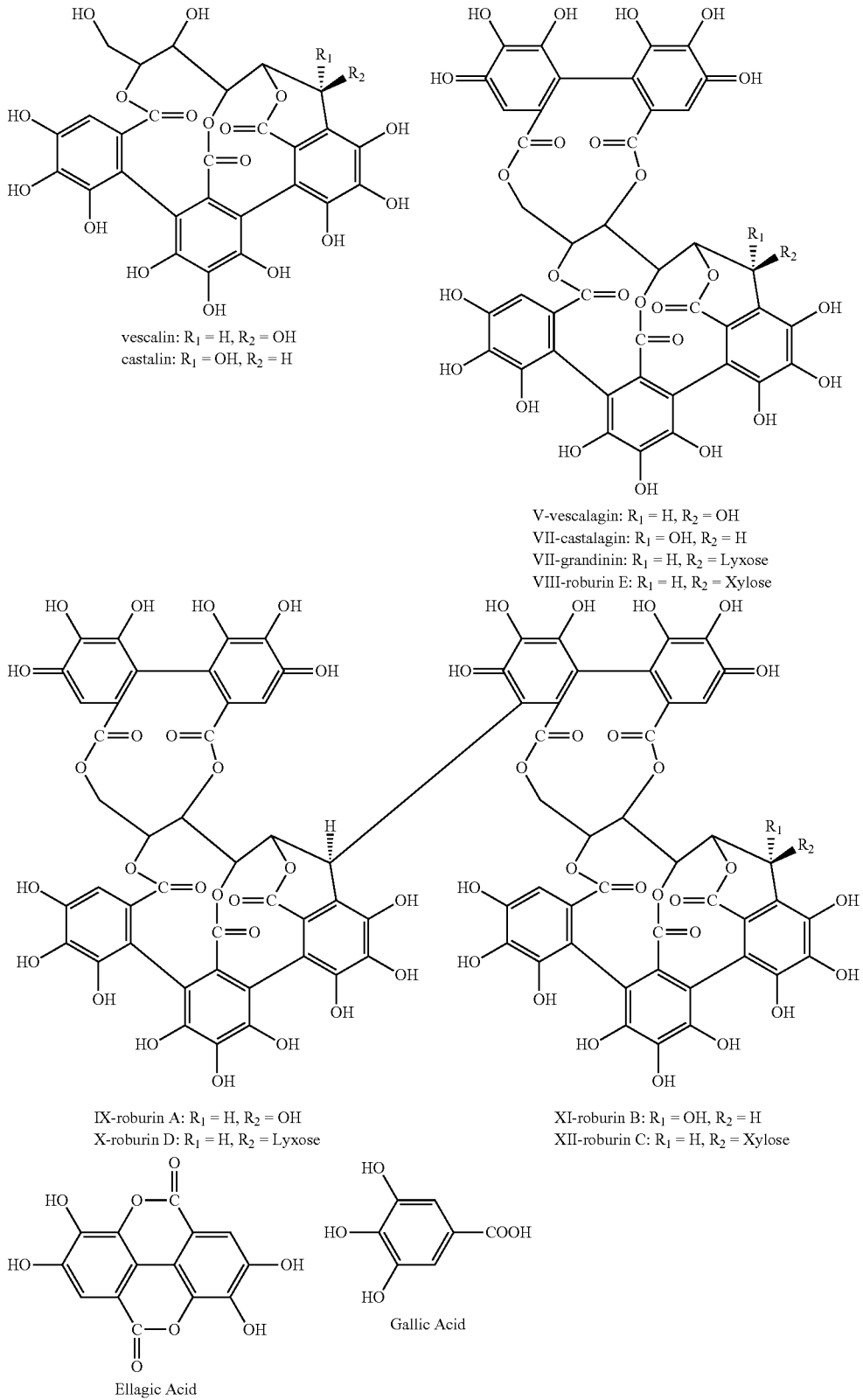

vescalin: $R_1$ = H, $R_2$ = OH
castalin: $R_1$ = OH, $R_2$ = H

V-vescalagin: $R_1$ = H, $R_2$ = OH
VII-castalagin: $R_1$ = OH, $R_2$ = H
VII-grandinin: $R_1$ = H, $R_2$ = Lyxose
VIII-roburin E: $R_1$ = H, $R_2$ = Xylose IX-roburin A: $R_1$ = H, $R_2$ = OH
X-roburin D: $R_1$ = H, $R_2$ = Lyxose XI-roburin B: $R_1$ = OH, $R_2$ = H
XII-roburin C: $R_1$ = H, $R_2$ = Xylose Ellagic Acid Gallic Acid The composition consisting of ellagitannins, present in the preparation of the invention, is originated from a plant extract or alternatively from a synthesized material (i.e., synthetic ellagitannins, i.e. roburins).

Ellagitannins containing rich extracts are natural and preferably plant extracts having more than 50% by weight (of dried extracts) of ellagitannins (in particular roburins), more preferably more than 70% by weight and even more preferably more than 75% by weight of ellagitannins (in particular roburins). Preferably the plant extract according to the present invention is originated from oak wood extracts and more preferably the plant extract is *Quercus robur*.

In a preferred embodiment, the composition may contain ellagitannins (in particular roburins) at a concentration of 10% to 100% of total weight. For example, the composition of the invention may be diluted or concentrated to contain 10%, 20%, 30%, 40%, 50%, 60%, 70%, 75%, 80%, 90% or 95% ellagitannins (in particular roburins). Concentration may be performed using known methods such as column chromatography or affinity chromatography.

The composition of the invention may further comprise vitamins, coenzymes, mineral substances, aminoacids and antioxidants and/or a suitable excipient q.s.p. The composition may be manufactured in the form of tablets, lozenges, capsules, pills, granulates, syrups, vials or drops.

The suitable excipient of the invention is an acceptable excipient or carrier as defined above.

Examples of suitable excipients of this invention include, but are not limited to, anti-adherents, binders (e.g., macrocrystalline cellulose, gum tragacanth, or gelatin), coatings, disintegrants, fillers, diluents, softeners, emulsifiers, flavoring agents, coloring agents, adjuvants, lubricants, functional agents (e.g., nutrients), viscosity modifiers, bulking agents, glidiants (e.g., colloidal silicon dioxide) surface active agents, osmotic agents, diluents, or any other non-active ingredient, or combinations thereof.

For example, the composition of the present invention may further include excipient materials selected from the group consisting of calcium carbonate, coloring agents, whiteners, preservatives, and flavors, triacetin, magnesium stearate, sterotes, natural or artificial flavors, essential oils, plant extracts, fruit essences, gelatins, or combinations thereof.

Optionally the composition of the present invention may include other artificial or natural sweeteners, bulk sweeteners, or combinations thereof. Bulk sweeteners include both caloric and non-caloric compounds. Non-limiting examples of bulk sweeteners include sucrose, dextrose, maltose, dextrin, dried invert sugar, fructose, high fructose corn syrup, levulose, galactose, corn syrup solids, tagatose, polyols (e.g., sorbitol, mannitol, xylitol, lactitol, erythritol, and maltitol), hydrogenated starch hydrolysates, isomalt, trehalose, and combinations thereof.

In a preferred embodiment of the invention, the suitable excipient is a pharmaceutically acceptable excipient.

The present invention further provides for a food preparation, a dietary or food supplement, a nutraceutical, a beverage, a medicament and a topical preparation comprising the composition of the present invention.

Preferably, the dietary supplement, the nutraceutical or the medicament of the present invention is administered at a dosage of between 5 mg per day to 2,000 mg per day. Preferably between 50 mg to 1,000 mg per day and even more preferably between 100 mg to 400 mg per day.

The preparation, the dietary supplement, the nutraceutical or the medicament of the present invention can be administered orally, parenterally or topically at a dosage of between 5 mg per day to 2,000 mg per day. Preferably between 50 mg to 1,000 mg per day and more preferably between 100 mg to 400 mg per day.

If intended for oral administration, the medicament of the present invention can be in the form, for example, of a tablet, a caplet, a pill, a hard or soft capsule, a lozenge, a cachet, a dispensable powder, granules, a suspension, an elixir, a dispersion, a liquid, or any other form reasonably adapted for such administration. If intended for parenteral administration, it can be in the form, for example, of a solution for intravenous, intramuscular or subcutaneous injection.

The topical preparations according to the present invention can be, but not limited to, a cream, a patch, a gel, an ointment, a lotion, a tincture, a spray, a mousse, a cleansing composition or a foam. The topical preparations of the present invention can be also in the form of a suspension or dispersion in solvents or fatty substances, or alternatively in the form of an emulsion or micro emulsion, PET-emulsions, multiple emulsions, bickering emulsions, hydrogels, alcoholic gels, lipogels, one or multiphase solutions or a vesicular dispersion and other usual compositions, which can also be applied by pens, as masks or as sprays. The emulsions can also contain anionic, nonionic, cationic or amphoteric surfactant(s).

The composition of the invention may be used in a food preparation, a dietary supplement, a medicament, a nutraceutical, or a beverage.

Preferably, the composition or the medicament of the invention is administered orally, parenterally or topically as defined above.

An oral administration of the blend in accordance with an administration regimen over a prolonged period of time provides certain benefits, which include helping to protect, restore and sustain blood vessel health and improve blood flow to the genital area, naturally enhancing male erections or female tumescence, naturally enhancing the body's sexual response and improving the health of the sexual vascular system.

By orally administering the composition of the invention, the benefits to sexual fitness or sexual wellness are realized. That is, over time, the cumulative effect of the blend leaves one experiencing a heightened sense of sexual well-being.

The blend or composition of the present invention may be in the form of a composition, taken either in tablet form or in liquid form. Alternatively, the blend may be in the form of the ingredients being in separate, distinct tablet or liquid form but packaged together in a kit. In the latter case, the separate ingredients are taken either simultaneously, such as by mixing them together if in liquid form, or one after another if in tablet form.

In one embodiment of the invention, the composition or the medicament of the invention is administered at a dosage of between 5 mg per day to 2,000 mg per day. The subject in need thereof is a mammal, preferably a human.

The medicament or the dietary supplement of the invention is for example adapted for use in improving sexual fitness or wellness of both sexes, for use in improving man sexual enhancement such as sperm production or fertility and/or for use in treating or preventing sexual dysfunction in both sexes.

The latter composition is for example adapted for use in improving sexual fitness or wellness of both sexes, for use in improving man and female sexual enhancement and/or for use in treating or preventing sexual dysfunction in both sexes.

A unit dosage comprises a therapeutically effective daily amount of the composition of the invention which may be taken as a single daily administration or by multiple small doses taken over the course of a day.

Also encompassed is a kit comprising the composition of the invention.

Those skilled in the art will appreciate that the invention described herein is susceptible to variations and modifications other than those specifically described. It is to be understood that the invention includes all such variations and modifications without departing from the spirit or essential characteristics thereof. The invention also includes all of the steps, features, compositions and compounds referred to or indicated in this specification, individually or collectively, and any and all combinations or any two or more of said steps or features. The present disclosure is therefore to be considered as in all aspects illustrated and not restrictive, the scope of the invention being indicated by the appended Claims, and all changes which come within the meaning and range of equivalency are intended to be embraced therein.

Various references are cited throughout this specification, each of which is incorporated herein by reference in its entirety.

The foregoing description will be more fully understood with reference to the following Examples. Such Examples, are, however, exemplary of methods of practicing the present invention and are not intended to limit the scope of the invention.

EXAMPLES

Example 1

1). QR Extract for Improvement of Female Sexual Function

The female sexual function was used to assess sexual function in women. Women's sexual function is scored using the established "Female Sexual Function Index" (FSFI) questionnaire [Rosen R, Brown C, Heiman J, Leiblum S, Meston C M, Shabsigh R, Ferguson D, D'Agostino R., Jr *The Female Sexual Function Index (FSFI): A multidimensional self-report instrument for the assessment of female sexual function. Journal of Sex & Marital Therapy.* 2000; 26:191-208].

The questionnaire allows to score prevalence of six sub-categories (domains) related to female sexual function, with minimum and maximum scores given:

| | |
|---|---|
| Desire | 1.2-6 |
| Arousal | 0-6 |
| Lubrication | 0-6 |
| Satisfaction | 0.8-6 |
| Pain | 0-6 |
| Orgasm | 0-6 |

FSFI SCORING APPENDIX

| Question | Response Options |
|---|---|
| 1. Over the past 4 weeks, how often did you feel sexual desire or interest? | 5 = Almost always or always<br>4 = Most times (more than half the time)<br>3 = Sometimes (about half the time)<br>2 = A few times (less than half the time)<br>1 = Almost never or never |
| 2. Over the past 4 weeks, how would you rate your level (degree) of sexual desire or interest? | 5 = Very high<br>4 = High<br>3 = Moderate<br>2 = Low<br>1 = Very low or none at all |
| 3. Over the past 4 weeks, how often did you feel sexually aroused ("turned on") during sexual activity or intercourse? | 0 = No sexual activity<br>5 = Almost always or always<br>4 = Most times (more than half the time)<br>3 = Sometimes (about half the time)<br>2 = A few times (less than half the time)<br>1 = Almost never or never |
| 4. Over the past 4 weeks, how would you rate your level of sexual arousal ("turn on") during sexual activity or intercourse? | 0 = No sexual activity<br>5 = Very high<br>4 = High<br>3 = Moderate<br>2 = Low<br>1 = Very low or none at all |
| 5. Over the past 4 weeks, how confident were you about becoming sexually aroused during sexual activity or intercourse? | 0 = No sexual activity<br>5 = Very high confidence<br>4 = High confidence<br>3 = Moderate confidence<br>2 = Low confidence<br>1 = Very low or no confidence |
| 6. Over the past 4 weeks, how often have you been satisfied with your arousal (excitement) during sexual activity or intercourse? | 0 = No sexual activity<br>5 = Almost always or always<br>4 = Most times (more than half the time)<br>3 = Sometimes (about half the time)<br>2 = A few times (less than half the time)<br>1 = Almost never or never |
| 7. Over the past 4 weeks, how often did you become lubricated ("wet") during sexual activity or intercourse? | 0 = No sexual activity<br>5 = Almost always or always<br>4 = Most times (more than half the time)<br>3 = Sometimes (about half the time)<br>2 = A few times (less than half the time)<br>1 = Almost never or never |
| 8. Over the past 4 weeks, how difficult was it to become lubricated ("wet") during sexual activity or intercourse? | 0 = No sexual activity<br>1 = Extremely difficult or impossible<br>2 = Very difficult<br>3 = Difficult<br>4 = Slightly difficult<br>5 = Not difficult |
| 9. Over the past 4 weeks, how often did you maintain your lubrication ("wetness") until completion of sexual activity or intercourse? | 0 = No sexual activity<br>5 = Almost always or always<br>4 = Most times (more than half the time)<br>3 = Sometimes (about half the time)<br>2 = A few times (less than half the time)<br>1 = Almost never or never |
| 10. Over the past 4 weeks, how difficult was it to maintain your lubrication ("wetness") until completion of sexual activity or intercourse? | 0 = No sexual activity<br>1 = Extremely difficult or impossible<br>2 = Very difficult<br>3 = Difficult<br>4 = Slightly difficult<br>5 = Not difficult |
| 11. Over the past 4 weeks, when you had sexual stimulation or intercourse, how often did you reach orgasm (climax)? | 0 = No sexual activity<br>5 = Almost always or always<br>4 = Most times (more than half the time)<br>3 = Sometimes (about half the time)<br>2 = A few times (less than half the time)<br>1 = Almost never or never |
| 12. Over the past 4 weeks, when you had sexual stimulation or intercourse, how difficult was it for you to reach orgasm (climax)? | 0 = No sexual activity<br>1 = Extremely difficult or impossible<br>2 = Very difficult<br>3 = Difficult<br>4 = Slightly difficult<br>5 = Not difficult |

| 13. Over the past 4 weeks, how satisfied were you with your ability to reach orgasm (climax) during sexual activity or intercourse? | 0 = No sexual activity<br>5 = Very satisfied<br>4 = Moderately satisfied<br>3 = About equally satisfied and dissatisfied<br>2 = Moderately dissatisfied<br>1 = Very dissatisfied |
|---|---|
| 14. Over the past 4 weeks, how satisfied have you been with the amount of emotional closeness during sexual activity between you and your partner? | 0 = No sexual activity<br>5 = Very satisfied<br>4 = Moderately satisfied<br>3 = About equally satisfied and dissatisfied<br>2 = Moderately dissatisfied<br>1 = Very dissatisfied |
| 15. Over the past 4 weeks, how satisfied have you been with your sexual relationship with your partner? | 5 = Very satisfied<br>4 = Moderately satisfied<br>3 = About equally satisfied and dissatisfied<br>2 = Moderately dissatisfied<br>1 = Very dissatisfied |
| 16. Over the past 4 weeks, how satisfied have you been with your overall sexual life? | 5 = Very satisfied<br>4 = Moderately satisfied<br>3 = About equally satisfied and dissatisfied<br>2 = Moderately dissatisfied<br>1 = Very dissatisfied |
| 17. Over the past 4 weeks, how often did you experience discomfort or pain during vaginal penetration? | 0 = Did not attempt intercourse<br>1 = Almost always or always<br>2 = Most times (more than half the time)<br>3 = Sometimes (about half the time)<br>4 = A few times (less than half the time)<br>5 = Almost never or never |
| 18. Over the past 4 weeks, how often did you experience discomfort or pain following vaginal penetration? | 0 = Did not attempt intercourse<br>1 = Almost always or always<br>2 = Most times (more than half the time)<br>3 = Sometimes (about half the time)<br>4 = A few times (less than half the time)<br>5 = Almost never or never |
| 19. Over the past 4 weeks, how would you rate your level (degree) of discomfort or pain during or following vaginal penetration? | 0 = Did not attempt intercourse<br>1 = Very high<br>2 = High<br>3 = Moderate<br>4 = Low<br>5 = Very low or none at all |

FSFI DOMAIN SCORES AND FULL SCALE SCORE

The individual domain scores and full scale (overall) score of the FSFI can be derived from the computational formula outlined in the table below. For individual domain scores, add the scores of the individual items that comprise the domain and multiply the sum by the domain factor (see below). Add the six domain scores to obtain the full scale score. It should be noted that within the individual domains, a domain score of zero indicates that the subject reported having no sexual activity during the past month. Subject scores can be entered in the right-hand column.

| Domain | Questions | Score Range | Factor | Minimum Score | Maximum Score | Score |
|---|---|---|---|---|---|---|
| Desire | 1, 2 | 1 – 5 | 0.6 | 1.2 | 6.0 | |
| Arousal | 3, 4, 5, 6 | 0 – 5 | 0.3 | 0 | 6.0 | |
| Lubrication | 7, 8, 9, 10 | 0 – 5 | 0.3 | 0 | 6.0 | |
| Orgasm | 11, 12, 13 | 0 – 5 | 0.4 | 0 | 6.0 | |
| Satisfaction | 14, 15, 16 | 0 (or 1) – 5 | 0.4 | 0.8 | 6.0 | |
| Pain | 17, 18, 19 | 0 – 5 | 0.4 | 0 | 6.0 | |
| | | Full Scale Score Range | | 2.0 | 36.0 | |

Adult women of all ages were investigated who presented with a score lower than four points out of maximum six points for all six domains.

The investigation depicts the number of responders to the intervention as detailed in table 8 after four week treatment with a score equal to or higher than four points for all six domains.

TABLE 8

| Dosage of QR extract | Number of women responding | Total number of women investigated |
| --- | --- | --- |
| 0 mg | 0 | 22 |
| 50 mg | 5 | 23 |
| 100 mg | 11 | 24 |
| 200 mg | 16 | 22 |
| 300 mg | 21 | 25 |

Conclusions:

The results show that QR extract has a dose-related efficacy in improving sexual function in women. The efficacy increased with the dosage.

In addition it was observed that the individual six FSFI domains related to desire, arousal, lubrication, orgasm, satisfaction and pain did all respond favourably to treatment with QR and the improvement of the scores were related to the dosage.

2). QR Extract for Improvement of Male Sexual Function

Men's sexual function is scored using the established "International Index of Erectile Function" (IIEF) questionnaire [Rosen et ah, *Urology.* 1997 June; 49(6):822-30. *The international index of erectile function (IIEF): a multidimensional scale for assessment of erectile dysfunction*]. A subset of only 6 questions (1-5 plus 15) of the total 30 questions is related to erectile function with values ranging from minimum zero to 30.

IIEF scores range from [0-30].

Over the past four weeks:

1. How often were you able to get an erection during sexual activity? _____

0 = No sexual activity
   1 = Almost never/never
   2 = A few times (much less than half the time)
   3 = Sometimes (about half the time)
   4 = Most times (much more than half the time)
   5 = Almost always/always 2. When you had erections with sexual stimulation, how often were your erections hard enough for penetration? _____

0 = No sexual activity
   1 = Almost never/never
   2 = A few times (much less than half the time)
   3 = Sometimes (about half the time)
   4 = Most times (much more than half the time)
   5 = Almost always/always 3. When you attempted sexual intercourse, how often were you able to penetrate (enter) your partner? _____

0 = Did not attempt intercourse
   1 = Almost never/never
   2 = A few times (much less than half the time)
   3 = Sometimes (about half the time)
   4 = Most times (much more than half the time)
   5 = Almost always/always 4. During intercourse, how often were you able to maintain your erection after you had penetrated (entered) your partner? _____

0 = Did not attempt intercourse
   1 = Almost never/never
   2 = A few times (much less than half the time)
   3 = Sometimes (about half the time)
   4 = Most times (much more than half the time)
   5 = Almost always/always 5. During sexual intercourse, how difficult was it to maintain your erection to completion of intercourse? _____

0 = Did not attempt intercourse
   1 = Extremely difficult
   2 = Very difficult
   3 = Difficult
   4 = Slightly difficult
   5 = Not difficult 6. How many times have you attempted sexual intercourse? _____

0 = No attempts
   1 = One to two attempts
   2 = Three to four attmepts
   3 = Five to six attempts
   4 = Seven to ten attempts
   5 = Eleven or more attempts 7. When you attempted sexual intercourse, how often was it satisfactory for you? _____

0 = Did not attempt intercourse
1 = Almost never/never
2 = A few times (much less than half the time)
3 = Sometimes (about half the time)
4 = Most times (much more than half the time)
5 = Almost always/always 8. How much have you enjoyed sexual intercourse? _____

0 = No intercourse
1 = No enjoyment
2 = Not very enjoyable
3 = Fairly enjoyable
4 = Highy enjoyable
5 = Very highly enjoyable 9. When you had sexual stimulation or intercourse, how often did you ejaculate? _____

0 = No sexual stimulation/intercourse
1 = Almost never/never
2 = A few times (much less than half the time)
3 = Sometimes (about half the time)
4 = Most times (much more than half the time)
5 = Almost always/always 10. When you had sexual stimulation or intercourse, how often did you have the feeling of orgasm or climax? _____

0 = No sexual stimulation/intercourse
1 = Almost never/never
2 = A few times (much less than half the time)
3 = Sometimes (about half the time)
4 = Most times (much more than half the time)
5 = Almost always/always 11. How often have you felt sexual desire? _____

1 = Almost never/never
2 = A few times (much less than half the time)
3 = Sometimes (about half the time)
4 = Most times (much more than half the time)
5 = Almost always/always 12. How would you rate your sexual desire? _____

1 = Very low/none at all
2 = Low
3 = Moderate
4 = High
5 = Very high

13. How satisfied have you been with your overall sex life? _____

1 = Very dissatisfied
2 = Moderately dissatisfied
3 = About equally satisfied and dissatisfied
4 = Moderately satisfied
5 = Very satisfied 14. How satisfied have you been with your sexual relationship with your partner? _____

1 = Very dissatisfied
2 = Moderately dissatisfied
3 = About equally satisfied and dissatisfied
4 = Moderately satisfied
5 = Very satisfied 15. How would you rate your confidence that you could get and keep an erection? _____

1 = Very low
2 = Low
3 = Moderate
4 = High
5 = Very high

Men entering the study are having moderate erectile problems at baseline with values 13-18 and after treatment achieving sufficient erectile abilities (values of 19 and above). Treatment duration was 2 weeks.

Number of men responding with IIEF ≥19 at different QR extract dosages taken for two weeks:

TABLE 9

| Dosage of QR extract | Number of men responding with IIEF ≥ 19 | Total number of men investigated |
|---|---|---|
| 0 mg | 0 | 23 |
| 50 mg | 6 | 25 |
| 100 mg | 10 | 22 |
| 200 mg | 15 | 22 |
| 300 mg | 20 | 26 |

Conclusions:

The results show that QR extract has a dose-related efficacy in improving sexual function in men. The efficacy increased with the dosage.

In parallel to the increase of erectile function, the number or intercourse increased significantly. The detailed IIEF scores for orgasmic function, sexual desire, intercourse satisfaction and overall satisfaction were significantly increased.

The invention claimed is:

1. A method for treating sexual dysfunction in a subject in need thereof, the method comprising administering to the subject an effective amount of a composition consisting of an extract of a plant of the genus *Quercus*, wherein said extract has more than 10% w/w of ellagitannins based on dried extract.

2. The method of claim 1, wherein the extract comprises Roburins.

3. The method of claim 1, wherein the extract is selected from the group consisting of extracts from wood, bark, fruit, roots, or leaves.

4. The method of claim 3, wherein the plant is *Quercus robur*.

5. The method of claim 1, wherein the composition is in a form adapted for oral administration.

6. The method of claim 5, wherein the composition is in the form of a food preparation, a dietary supplement, a nutraceutical, or a beverage.

7. The method of claim 1, wherein the subject is a male or female human.

8. The method of claim 2, wherein the Roburins are selected from the group consisting of Roburins A, B, C, D, and E.

9. The method of claim 3, wherein the plant is selected from *Quercus alba*, *Quercus brutia* Tenore, *Quercus pedunculiflora*, *Quercus haas*, *Quercus petraea* and *Quercus robur*.

10. A method for improving sexual fitness or wellness or sexual enhancement in a subject in need thereof, the method comprising administering to the subject an effective amount of a composition consisting of an extract from a plant of the genus *Quercus*, wherein said extract has more than 10% w/w of ellagitannins based on dried extract.

11. The method according to claim 10, wherein the extract comprises Roburins.

12. The method of claim 10, wherein the extract is selected from the group consisting of extracts from wood, bark, fruit, roots, or leaves.

13. The method of claim 10, wherein the plant is *Quercus robur*.

14. The method of claim 10, wherein the subject is a male or female human.

15. The method of claim 11, wherein the Roburins are selected from the group consisting of Roburins A, B, C, D, and E.

16. A method for improving the health of the sexual vascular system in a subject in need thereof, the method comprising administering to the subject an effective amount of a composition consisting essentially of an extract of a plant of the genus *Quercus*, wherein said extract has more than 10% w/w of ellagitannins based on dried extract.

17. The method of claim 16, wherein when administered said composition offers a safe, natural way to preserve and maintain sexual responsiveness, endurance and enjoyment.

18. The method of claim 16, wherein the subject is a male or female human.

19. The method of claim 16, wherein the extract comprises a Roburin selected from the group consisting of Roburins A, B, C, D, and E.

* * * * *